United States Patent [19]

Danilewicz et al.

[11] 4,001,422
[45] Jan. 4, 1977

[54] 4-AMINOQUINAZOLINE CARDIAC STIMULANTS

[75] Inventors: John C. Danilewicz, Ash; Anthony G. Evans, Sandwich; Allan L. Ham, Broadstairs; Colin Thomson, Sandwich, all of England

[73] Assignee: Pfizer Inc., New York, N.Y.

[22] Filed: July 24, 1975
(Under Rule 47)

[21] Appl. No.: 598,723

[30] Foreign Application Priority Data

July 25, 1974 United Kingdom ............. 32805/74
Jan. 6, 1975 United Kingdom ................. 416/75

[52] U.S. Cl. .......................... 424/251; 260/256.4 Q
[51] Int. Cl.² ................. A01N 9/22; C07D 239/72
[58] Field of Search ............ 260/256.4 Q; 424/251

[56] References Cited
UNITED STATES PATENTS

| | | | |
|---|---|---|---|
| 3,511,836 | 5/1970 | Jurger et al. | 260/256.4 Q |
| 3,517,005 | 6/1970 | Cronin et al. | 260/256.4 Q |

FOREIGN PATENTS OR APPLICATIONS

| | | | |
|---|---|---|---|
| 2,220,265 | 4/1974 | France | 260/256.4 Q |
| 2,121,031 | 11/1972 | Germany | 260/256.4 Q |

OTHER PUBLICATIONS

Scarborough et al., J. Org. Chem., 27, 957 (1961).

*Primary Examiner*—Lewis Gotts
*Assistant Examiner*—D. R. Phillips
*Attorney, Agent, or Firm*—Connolly and Hutz

[57] ABSTRACT

6,7-Dialkoxy-4-aminoquinazoline cardiac stimulants and synthetic methods for the preparation thereof.

24 Claims, No Drawings

4-AMINOQUINAZOLINE CARDIAC STIMULANTS

BACKGROUND OF THE INVENTION

1. Field of the Invention

This invention relates to therapeutic agents and, in particular, to novel 4-aminoquinazoline derivatives useful as cardiac stimulants.

2. Description of the Prior Art

Quinazolines are a well-known class of organic compounds, some of which are reported to have useful therapeutic properties. U.S. Pat. No. 3,517,005 discloses 4-aminoquinazoline derivatives with hypotensive and bronchodilator activity, and U.S. Pat. No. 3,511,836 reports hypotensive activity for 2,4-diaminoquinazolines. Scarborough et al., J. Org. Chem., 27,957 (1961) reports the preparation of several 4-(1-substituted 3-pyrrolidinylmethylamino)-quinazolines. Belgium Patent 811,856 teaches the use of 4-(N-heterocyclicalkylamino)quinazolines as cardiac stimulants.

SUMMARY OF THE INVENTION

It has now been found that certain 6,7-dialkoxy-4-aminoquinazolines and their pharmaceutically acceptable acid addition salts are outstandingly active as cardiac stimulants.

A preferred group of compounds and their pharmaceutically acceptable acid addition salts are of the formula

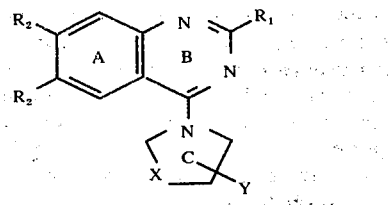

wherein $R_1$ is hydrogen or alkyl of one to three carbon atoms; $R_2$ is alkoxy of one to two carbon atoms; X is —CH=CH—, —CH$_2$CH=CH— or alkylene of one to three carbon atoms; and Y is a 3- or 4-substituent in ring C from the group —Z$_1$COR$_3$, —N(R$_4$)SO$_2$R$_5$, —Z$_2$-CONR$_6$R$_7$ or —Z$_2$CSNR$_6$R$_7$ wherein $Z_1$ is —CH$_2$—or —N(R$_4$)—; $R_3$ is alkyl of one to four carbon atoms, alkoxy of one to four carbon atoms, benzyoxy, phenoxy, ethoxycarbonylmethyl or pyridyl; $R_5$ is alkyl of one to four carbon atoms, pyridyl or —NR$_6$R$_7$; $Z_2$ is —O—, —CH$_2$— or —N(R$_4$)— wherein R$_4$ is hydrogen, pyridyl, phenyl, alkyl of one to four carbon atoms or substituted said alkyl wherein the substituent is amino, dimethylamino, hydroxy, pyridyl or phenyl; and R$_6$ and R$_7$ when considered separately are hydrogen or alkyl of one to four carbon atoms and R$_6$ and R$_7$ when considered together with the nitrogen to which they are attached form a piperidine ring, with the proviso that when X is —CH=CH— or —CH$_2$CH=CH— Y is —CH$_2$COR$_3$, CH$_2$COR$_3$, CH$_2$CONR$_6$R$_7$ or —CH$_2$CSNR$_6$R$_7$.

A class of especially preferred compounds are those wherein $R_1$ is hydrogen, $R_2$ is methoxy, X is —CH$_2$CH$_2$— and Y is a substituent at the 4-position of ring C.

Within this especially preferred class is a preferred group wherein Y is Z$_1$COR$_3$ wherein Z$_1$ is —N(R$_4$)— wherein R$_4$ is hydrogen or alkyl of one to four carbon atoms and R$_3$ is alkyl or alkoxy each of one to four carbon atoms.

A second group within the especially preferred class are those wherein Y is —N(R$_4$)SO$_2$R$_5$ wherein R$_4$ is hydrogen or alkyl of one to four carbon atoms and R$_5$ is pyridyl or —NR$_6$R$_7$ wherein R$_6$ and R$_7$ when considered separately are hydrogen or alkyl of one to four carbon atoms and R$_6$ and R$_7$ when taken together with nitrogen to which they are attached form a piperidine ring.

A final group of compounds within the especially preferred class are those wherein Y is Z$_2$CONR$_6$R$_7$ wherein Z$_2$ —O— or —N(R$_4$)— wherein R$_6$ and R$_7$ when considered separately are each hydrogen or alkyl of one to four carbon atoms, and R$^4$ is hydrogen, alkyl of 1 to 4 carbon atoms or pyridyl-substituted said alkyl.

In a broader sense this invention is meant to include within its scope compounds of the formula

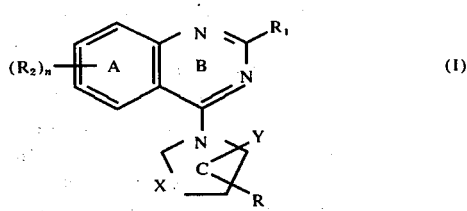

wherein $R_1$ is hydrogen or a lower alkyl group; $(R_2)_n$ represents 1 to 3 optional substituents, each R$_2$ being hydrogen, hydroxy or lower alkoxy, n being 1 to 3, or any two of the R$_2$ constitute a methylenedioxy or ethylenedioxy group attached to adjacent positions of ring A;

X represents —(CH$_2$)$_p$ wherein p is 1 to 3, —CH=CH— or —CH$_2$CH=CH—;

Y is attached to the 3- or 4-position of ring C and represents either:

a. a group of the formula —Z$_1$COR$_3$ wherein Z$_1$ is —CH$_2$—or —N(R$_4$)—, $R_3$ is lower alkyl group optionally substituted by an amino, hydroxy, lower alkoxy, aryl or heteroryl group; a lower alkenyl-or lower alkynylmethyl group; a lower alkoxy group optionally substituted by an amino, aryl, heteroaryl, lower alkoxy or hydroxyl group; an aryl group; an aryloxy group; or a heteroaryl group; and $R_4$ is a hydrogen atom; a lower alkyl group optionally substituted by an amino, lower alkoxy, hydroxy, carbethoxy, aryl or heteroaryl group; a lower alkenyl-or lower alkynylmethyl group; an aryl group or a heteroaryl group;

b. a group of the formula —N(R$_4$)SO$_2$R$_5$ wherein R$_5$ is defined as R$_3$ or is a group of the formula —NR$_6$R$_7$ which R$_7$ is a hydrogen or a lower alkyl group and R$_6$ is defined as R$_4$, or R$_6$ and R$_7$ taken together with the nitrogen to which they are attached form a saturated monocyclic heterocyclic ring; or c. a group of the formula

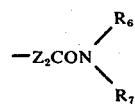

or —Z$_2$CSNR$_6$R$_7$ wherein Z$_2$ is Z$_1$ or —O—, and R$_6$ and R$_7$ are as defined provided that when Z$_2$ is —N(R$_4$)—, R$_4$ and R$_7$ taken together may represent —(CH$_2$)$_2$—, —(CH$_2$)$_3$— or an o - phenylenediamine group; and R is a hydrogen atom or a lower alkyl group attached to the same carbon atom as Y; provided that when X is —CH=CH— or —CH$_2$—CH=CH—, R is absent and Y is —CH$_2$COR$_3$, —CH$_2$CONR$_6$R$_7$ or —CH$_2$CSNR$_6$R$_7$ wherein R$_3$, R$_6$ and R$_7$ are as defined above, Y being attached to an unsaturated ring carbon atom; and their pharmaceutically acceptable acid addition salts.

The term "lower" applied an aklyl, alkenyl, alkynyl or alkoxy group indicates that such a group contains up to six carbon atoms, and such group may be straight or branched chain. "Aryl" and "heteroaryl" as used herein include unsaturated aryl and heteroaryl groups, and aryl and heteroaryl groups substituted by lower alkyl, lower alkoxy, hydroxy, halogen or acetamido groups.

By the term "amino" as used herein, is meant a group of the formula —NR$_8$R$_9$ wherein R$_8$ is hydrogen or lower alkyl, and R$_9$ is hydrogen, lower alkyl, or aryl substituted lower alkyl, or R$_8$R$_9$ taken together with the nitrogen atom to which they are attached form a saturated monocyclic heterocyclic group. "Halogen" means fluorine, chlorine, bromine or iodine.

Compounds of the claimed invention containing one or more asymmetric centres will exist as one or more pairs of enantiomers, and such pairs or individual isomers may be separable by physical methods, e.g. by fractional crystallization or chromatography of the free bases or suitable salts. The invention includes the separated pairs as well as mixtures thereof, as racemic mixtures or as separated D- and L-optically-active isomeric forms.

It should also be understood that compounds of the present invention in which ring C is unsaturated may exist in tautomeric forms:

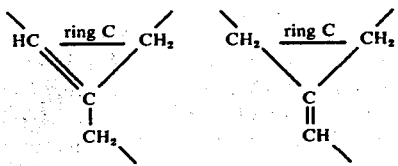

DETAILED DESCRIPTION OF THE INVENTION

The compounds of the present invention may be prepared by a number of routes:
Route A Compounds of the formula (I) may be prepared by reacting an appropriately substituted quinazoline of the formula:

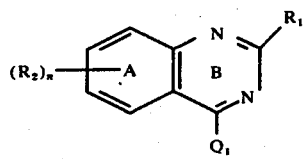

wherein Q$_1$ represents a leaving group such as chloro-, bromo-, iodo-, lower alkoxy or (lower alkyl) thio, with an amine of the formula:

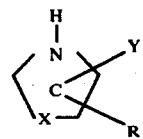

with resultant elimination of HQ$_1$. Q$_1$ is preferably chloro or bromo. The reaction is preferably carried out in an inert organic solvent such as ethanol or dimethylformamide with heating, e.g. under reflux, in a temperature range of 75° to 150° C. for one or more hours, generally 1 to 8 hours. When Q$_1$ is chloro-, bromo-, or iodo, the presence of a base such as triethylamine or of excess reagent of the formula (III) is advantageous.

Any substituent groups in the reactants capable of displacing the leaving group Q$_1$, other than the

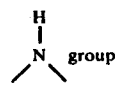

of the compound of the formula (III), i.e. hydroxy, primary amino and secondary amino groups, should generally be protected prior to the reaction by conventional methods, the protecting groups being removed after the reaction by standard procedures. Any hydroxy groups present may, if necessary, be protected by, for example, abenzyl group, which group may be removed after the reaction by hydrogenolysis. Any primary or secondary amino groups may, if necessary, be protected by, e.g. a benzyl or t-butoxy carbonyl group, which groups can be removed after the reaction by, respectively, hydrogenation or mild acid hydrolysis.

The product is typically isolated and purified by evaporation of the solvent in vacuo, followed by basification of the residue with a base such as aqueous sodium carbonate and extraction of the product into a suitable organic solvent, e.g. chloroform. After evaporation of the organic solvent, the crude product is left as a residue which is either converted to a salt and subsequently purified or recrystallized as the free base.
Route B Compounds of the formula (I) in which X is —(CH$_2$)p— and Y is —NR$_4$CONHR$_6$ or —NR$_4$CSNHR$_6$ may be prepared by reacting a quinazoline of the formula:

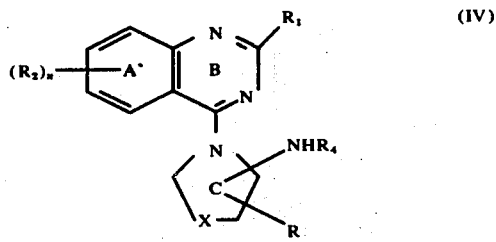

in which X is —(CH$_2$)p—, with either an isocyanate R$_6$NCO or isothiocyanate R$_6$NCS, R$_6$ being other than hydrogen, or, to prepare compounds wherein R$_6$ is H, sodium or potassium cyanate or thiocyanate in the presence of acid. To prepare compounds in which R$_6$ is other than hydrogen, the reaction is preferably carried out by allowing the reactants to stand together at room temperature for up to about 3 hours in an inert organic solvent such as chloroform. The product may then be isolated by evaporation of the solvent, and recrystallization of the thus-produced residue from a suitable solvent by normal methods. Alertnatively, the residue may be reacted with an acid to form a salt, and subsequently purified as such. To prepare compounds in which $R_6$ is hydrogen, the reactants are preferably heated together under reflux in a suitable solvent, e.g. aqueous ethanol, and in the presence of acid. The acid may be supplied by using and acid addition salt of the compound of the formula (IV) as the starting material.

Any groups capable of reacting with isocyanate or isothiocyanate groups or, as appropriate, with the cyanate or thiocyanate, other than of course the —NH— group of —$NHR_4$ in ring C, should generally be protected by conventional protecting groups prior to the reaction, the protecting group being removed by standard procedures after the reaction. Groups which it may be necessary to protect include hydroxy, primary amino and secondary amino groups, which groups may be present in $R_2$, $R_4$ and $R_6$.

Route C

Compounds of the formula (I) wherein X is —$(CH_2)p$— and Y is either —$NR_4COR_3$, —$NR_4SO_2R_5$ or -$NR_4CONR_6R_7$, may be prepared by reacting a compound of the formula (IV) as previously defined with, as appropriate, either:

a. a haloformate or acyl halide of the formula $Q_2COR_3$ wherein $Q_2$ is chloro or bromo;

b. a halosulfonate, sulfonyl halide or sulfamyl halide of the formula $Q_2SO_2R_5$, $Q_2$ being chloro or bromo;

c. a carbamyl halide of the formula $R_6R_7NCOQ_2$ wherein $R_6$ and $R_7$ are both other than hydrogen, and $Q_2$ is chloro or bromo;

or, d. an anhydride or pyrocarbonate of the formula $(R_3CO)_2O$.

Preferably the reactants are allowed to stand together at room temperature for a period of up to a few hours in an inert organic solvent, e.g. chloroform, in the presence of a base such as triethylamine.

Any groups in $R_2$ to $R_7$ capable of reacting with, or displacing as appropriate, the anhydride, pyrocarbonate or the group $Q_2$, e.g. hydroxy, primary amino, and secondary amino groups, should, if necessary, be protected prior to the reaction by conventional protecting groups which may be removed after the reaction by standard procedures.

The product is typically isolated and purified by the method described under Route A.

Route D

Compounds of the formula (I) wherein X is —$(CH_2)_p$— and Y is —$OCONHR_6$ or —$OCSNHR_6$ may be prepared by reacting a quinazoline of the formula:

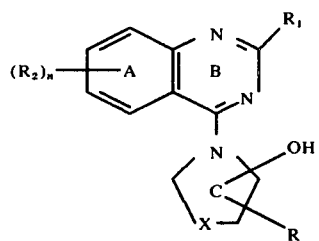

(V)

X being —$(CH_2)_p$—, with an isocyanate $R_6NCO$ or isothiocyanate $R_6NCS$, $R_6$ being other than hydrogen, or, to prepare compounds in which $R_6$ is hydrogen, sodium or potassium cyanate or thiocyanate in the presence of acid. Generally the reactants are heated together at temperatures of about 100° to 200° C in e.g. a stainless steel bomb for a period of about 24 to 48 hours in an inert organic solvent.

Any groups capable of reacting with isocyanate or isothiocyanate groups, or, as appropriate, with the cyanate or isocyanate, other than of course, the —OH group of ring C, should, if necessary, by protected prior to reaction e.g. in the same manner as that described under Route B. Similarly, the final product may typically be isolated by the method described under Route B.

Route E

Compounds of the formula (I) wherein X is —$(CH_2)_p$— and Y is —$NHCONR_6$— $R_7$ or —$NHCSNR_6R_7$ may be prepared by initially reacting a quinazoline of the formula:

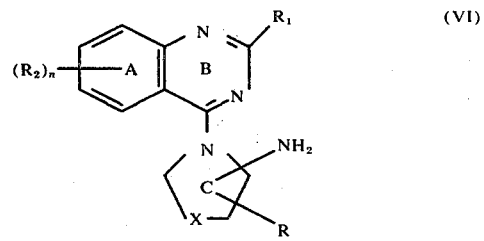

(VI)

X being —$(CH_2)_p$—, with phosgene $COCl_2$ or thiophosgene $CSCl_2$ in the presence of a base, e.g. triethylamine, and in the presence of an inert organic solvent such as chloroform or toluene, the —$NH_2$ group in ring C being converted to an —NCO or —NCS group. Generally strong stirring of the reaction mixture at room temperature is necessary, after which the mixture is allowed to stand for a few hours. A compound of the formula $R_6R_7NH$ is then added to the reaction mixture to react with the —NCO or —NCS group, the resulting mixture generally being allowed to stand for a few hours at room temperature to complete the reaction. If desired, the intermediate —NCO or —NCS-containing quinazoline may be isolated and optionally purified before reaction with the compound $R_6R_7NH$.

Any hydroxy groups, primary amino groups (other than, of course, the —$NH_2$ group of ring C), and secondary amino groups, should, if necessary, be protected by conventional protecting groups prior to the reaction, the groups being removed by standard procedures after the reaction.

The product may typically be isolated and purified by the procedure described under Route A.

Route F

Compounds of the formula (I) in which X is —$(CH_2)_p$— and Y is —$NR_4$— $COR_3$, $R_3$ being other than lower alkoxy, substituted lower alkoxy and aryloxy, may be prepared by reacting a quinazoline of the formula (V) as previously defined with an ester of N-hydroxy succinimide of the formula:

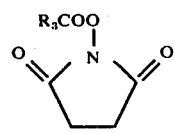

(VII)

in which $R_3$ is other than lower alkoxy, substituted alkoxy and aryloxy. The reaction is generally carried out by stirring the reactants together at room temperature in an inert organic solvent, e.g. dry chloroform, for a few hours.

Any hydroxy groups or primary or secondary amino groups in $R_2$ to $R_4$ should, if necessary, be protected prior to the reaction by conventional protecting groups which may be removed after the reaction by standard procedures.

The product may generally be isolated by the method described under Route A.

Route G

All compounds of the formula (I) wherein Y is —CH$_2$CONR$_6$R$_7$ may be prepared by reacting a compound of the formula:

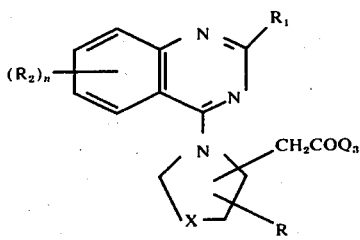

(VIII)

wherein $Q_3$ is a leaving group, such as a lower alkoxy, chloro-, or bromo-group, with a compound $R_6R_7NH$. The reactants are generally heated together neat, i.e. in the absence of any additional solvent, preferably in a closed stainless steel bomb at about 50° to 200° C for up to 48 hours. Heating may however not be necessary when $Q_3$ is a leaving group such as chloro or bromo. An inert organic solvent may however be added if required, and the presence of a base such as triethylamine or excess reagent $R_6R_7NH$ is advantageous when $Q_3$ is chloro or bromo.

Any substituent groups in $R_2$, $R_6$ and $R_7$ capable of reacting with the group —CH$_2$CO Q$_3$, e.g. primary or secondary amino groups, should, if necessary, be protected prior to reaction and de-protected after reaction.

The product is typically isolated and purified by the method described under Route A.

Route H

Compounds of the formula (I) in which X is —(CH$_2$)$_p$— and Y is —NR$_4$COR$_3$, $R_3$ being a lower alkyl group substituted by an amino group (as hereinbefore defined), may be prepared by reacting a quinazoline of the formula:

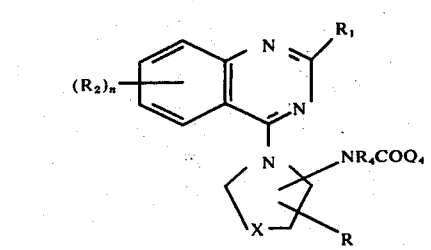

(IX)

X being —(CH$_2$)$_p$— and $Q_4$ being lower alkyl substituted by chloro- or bromo-, with a compound of the formula $R_8R_9NH$. Generally the reaction is carried out at room temperature in an inert organic solvent, e.g. chloroform, in the presence of a base such as triethylamine or excess compound $R_8R_9NH$, for a period of a few hours.

Any substituent groups in $R_2$ and $R_4$ capable of displacing the group $Q_4$, e.g. hydroxy and primary and secondary amino groups, should, if necessary, be protected prior to the reaction and de-protected after reaction.

The product is typically isolated and purified by the method described under Route A.

Route I

Compounds of the formula (I) wherein ring C is unsaturated and Y is thus —CH$_2$COR$_3$, —CH$_2$CONR$_6$R$_7$ or —CH$_2$CSNR$_6$R$_7$ may be prepared by reacting a quinazoline of the formula:

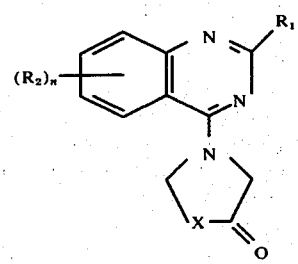

(X)

wherein X is —(CH$_2$)$_2$— or —(CH$_2$)$_3$—, with a phosphonate of the formula:

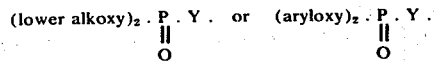

wherein Y is —CH$_2$COR$_3$, —CH$_2$CONR$_6$R$_7$ or —CH$_2$CSNR$_6$R$_7$. Generally the reaction is carried out at moderate temperatures for a period of up to a few hours, and in an inert organic solvent such as dimethoxyethane in the presence of a base, e.g. sodium hydride.

The product may be purified by the purification procedure described under Route B, and may be a mixture of tautomers.

Route J

All the compounds of the formula (I) in which Y is —CH$_2$CONR$_6$R$_7$ may be prepared by initially reacting a quinazoline of the formula:

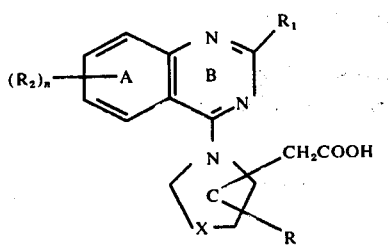

with a dehydrating agent such as di cyclohexylcarbodiimide, and N-hydroxy succinimide, to form an "activated" ester containing the grouping:

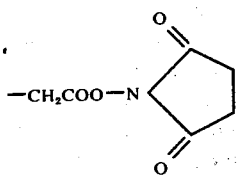

Preferably this reaction is carried out by allowing the reactants to stand together for a few hours at room temperature in an inert organic solvent, e.g. chloroform. A compound of the formula $R_6R_7NH$ is then added to the mixture to obtain the desired product, the mixture again generally being allowed to stand at room temperature for a few hours to complete the reaction. The reaction mixture is then filtered and the product recovered from the filtrate preferably via the isolation procedure described under Route B.

Any substituent groups in $R_2$ and $R_6$ capable of reacting with the —$CH_2COOH$ or activated ester group, e.g. primary and secondary amino groups, should, if necessary, be protected prior to the reaction and deprotected after reaction.

Acid addition salts of the compounds of formula (I) may be prepared from the crude or pure free base product by the conventional technique of reacting the free base with the acid in an inert solvent, e.g. by mixing alcoholic solutions of each and collecting the resulting precipitate by filtration. The product may then be recrystallized to purity.

In the above methods due regard should be had to the possibility that carbethoxy-substituted lower alkyl groups may be attacked by primary and secondary amino groups, and this should be borne in mind when preparing compounds in which $R_4$ or $R_6$ contain a carbethoxy group.

The 4-substituted quinazolines used as starting materials in the previous routes are either known compounds or are obtainable by analogous procedures to those of the prior art, such as British Patent Specification No. 1,199,768, or to those described in this specification. For example, the preparation of a compound of the formula IV from a ketone starting material of the formula X is described in part A of Example 10, and many other compounds of the formula IV are analogously obtainable. Furthermore, the preparation of a ketone starting material for this route is exemplified in part A of Example 91 and other such ketones are analogously obtainable. A route to the preparation of an amine of the formula VI is described in part A of Example 44, and other amines falling within this formula are analogously obtainable. An alternative route to the production of the amines of the formula VI could be via the catalytic hydrogenation of the corresponding compounds of the formula IV in which $R_4$ is a benzyl group. Also, many of the compounds of the formula VIII are obtainable via Route A described herein or analogously (Example 5 describes the preparation of a compound of the formula VIII wherein the "leaving group" $Q_3$ is an ethoxy group). Similarly, starting materials of the formula IX can generally be obtained analogously to Route C as described herein. Starting materials of the formula XI, which materials have a —$CH_2COOH$ group, are generally obtainable by hydrolysis of the corresponding ester, e.g. —$CH_2COOEt$, the ester being obtainable via Route I described herein when ring C is unsaturated, or via Route A when ring C is saturated.

As has been previously noted, compounds of the instant invention can form acid addition salts by virtue of the amino group. Basic compounds of the present invention are converted to the acid addition salts by interaction of the base with an acid either in an aqueous or non-aqueous medium. In a similar manner, treatment of the acid addition salts with an aqueous base solution, e.g., alkali metal hydroxides, alkali metal carbonates, and alkali metal bicarbonates to a basic pH or with a metal cation which forms an insoluble precipitate with the acid anion, results in a regeneration of the free base form. Such conversions are best carried out as rapidly as possible and under temperature conditions and method dictated by the stability of said basic products. The bases thus regenerated may be reconverted to the same or a different acid addition salt.

In the utilization of the chemotherapeutic activity of those compounds of the present invention which form acid addition salts, it is preferred, of course, to use pharmaceutically acceptable salts. Although water-insolubility, high toxicity, or lack of crystalline nature may make some particular salt species unsuitable or less desirable for use as such in a given pharmaceutical application, the water-insoluble or toxic salts can be converted to the corresponding pharmaceutically acceptable bases by decomposition of the salt as described above, or alternately they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phosphoric, acetic, lactic, citric, tartaric, succinic, maleic and gluconic.

The cardiac stimulant activity of the compounds of the invention is shown by their effectiveness in one or more of the following tests which have an excellent correlation with extrapilation to the effects in man: (a) increasing the force of contraction in the isolated, spontaneously beating, guinea pig double atria preparation; (b) increasing myocardial contractility (left ventricular $dP/d_t$max.) in the anesthetised dog with an implanted left ventricular catheter; (c) increasing myocardial contractility in the conscious dog with an implanted left ventricular transducer.

In test (a) the positive inotropic and chronotropic responses of the atria to the test compound are measured at several doses and compared with the responses elicited by isoprenaline. The comparison of the dose response curves obtained gives a measure of the force versus rate selectivity of the test compound.

In test (b) the positive inotropic action of the test compound following intravenous administration is measured in the anaesthetised dog and compared with that of isoprenaline. The potency of the inotropic action, the selectivity for increase in force versus frequency of contraction, and the duration of action of the positive inotropic effect of the test compound are obtained, as are its peripheral effects, e.g. the effect on the blood pressure.

In test (c) the positive inotropic action of the test compound following intravenous or oral administration to a conscious dog with an implanted left ventricular transducer is measured and compared with that of isoprenaline. The potency of the inotropic action, the selectivity for increase in force versus frequency of contraction, and the duration of action of the inotropic effect of the test compound are all obtained.

By virtue of the performance of the compounds of the invention in the above tests, the preferred compounds have been found to be as follows:

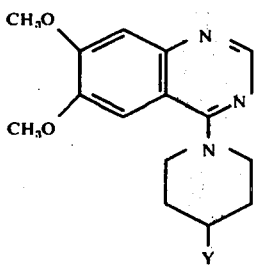

wherein Y is:

(a) —NHCONH(CH$_2$)$_3$CH$_3$, i.e., 4-(4-{3-n-butyl-ureido}-piperidino)-6,7-dimethoxyquinazoline, (b) —N(CH$_3$).CONH(CH$_2$)$_2$CH$_3$, i.e., 4-[4-{1-methyl-3-n-propyl-ureido}-piperidino]-6,7-dimethoxyquinazoline (c) —NHCOOCH$_2$CH$_3$, i.e., 4-[4-{ethoxycarbonylamino}piperidino]-6,7-dimethoxyquinazoline (d) —O.CONHCH$_2$CH$_3$, i.e., 4-[4-{ethylcarbamoyloxy}piperidino]-6,7-dimethoxyquinazoline (e) —N(CH$_3$).SO$_2$NH(CH$_2$)$_2$CH$_3$, i.e., 4-[4-{N-methyl-N-(n-propylsulfamoyl)-amino}piperidino]-6,7-dimethoxyquinazoline (f) —N(CH$_3$).COOCH$_2$CH$_3$, i.e., 4-[4-{N-methyl-N-ethoxycarbonylamino}-piperidino]-6,7-dimethoxyquinazoline (g) —NHCOOCH$_2$CH(CH$_3$)$_2$, i.e., 4-[4-{iso-butoxycarbonylamino}piperidino]-6,7-dimethoxyquinazoline (h) —NHCOO(CH$_2$)$_2$CH$_3$, i.e., 4-[4-{n-propoxycarbonylamino}piperidino]-6,7-dimethoxyquinazoline (i) —N(Et).COOEt, i.e., 4-[4{N-ethyl-N-ethoxycarbonylamino}piperidino]-6,7-dimethoxyquinazoline (j) —N . CONH(CH$_2$)$_3$CH$_3$, i.e., 4-[4-{3-n-butyl-1-(2-pyrid-4-yl-ethyl)-ureido}piperidino]-6,7-dimethoxyquinazoline
  |
 CH$_2$CH$_2$ . (4-pyridyl)

(k) —N . CONHCH$_3$, i.e. 4-[4-{3-methyl-1-n-propyl-ureido} piperidino]-6,7-dimethoxyquinazoline
  |
 (CH$_2$)$_2$CH$_3$ (l) —NCONH(CH$_2$)$_3$CH$_3$, i.e. 4-[4-{1,3-di-n-butyl-ureido} piperidino]-6,7-dimethoxyquinazoline
  |
 (CH$_2$)$_3$CH$_3$ (m) —OCONH(CH$_2$)$_2$CH$_3$, i.e. 4-[4-{n-propylcarbamoyloxy}piperidino]-6,7-dimethoxyquinazoline (n) —NHSO$_2$NH(CH$_2$)$_2$CH$_3$, i.e. 4-[4-{N-(n-propylsulfamoyl)amino}-piperidino]-6,7-dimethoxyquinazoline (o) —NHSO$_2$.(3-pyridyl), i.e. 4-[4-{3-pyridinesulfonamido}piperidino]-6,7-dimethoxyquinazoline (p) —N·SO$_2$·(3-pyridyl), i.e. 4-[4-{N-methyl-3-pyridinesulfon}-amido piperidino]-6,7-dimethoxyquinazoline
  |
 CH$_3$ (q) —NCO(CH$_2$)$_2$CH$_3$, i.e. 4-[4-{N-methylbutyramido}piperidino]-6,7-dimethoxyquinazoline
  |
 CH$_3$ and (r) —NHCO(CH$_2$)$_2$CH$_3$, i.e. 4-[4-{butyramido}piperidino]-6,7-dimethoxyquinazoline.

The compounds of the invention can be administered alone but will generally be administered in admixture with a pharmaceutical carrier selected with regard to the intended route of administration and standard pharmaceutical practice. For example they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylatic treatment of cardiac conditions such as congestive heart failure, it is expected that oral dosages of the most active compounds of the invention will be in the range from about 20 mg. to 1g. daily, taken in 2 to 4 divided doses per day, for an average adult patient (70 kg.). Dosages for intravenous administration would be expected to be within the range 1 to 300 mg. per single dose as required, for example in the treatment of acute heart failure. Thus for a typical adult patient, individual tablets or capsules might contain from about 5 to 500 mg. of active compound, in a suitable pharmaceutically-acceptable vehicle or carrier.

Thus the present invention provides a pharmaceutical composition comprising a compound of the formula (I) as defined above together with a pharmaceutically acceptable carrier.

The following examples are provided solely for the purpose of illustration and are not to be construed as limitations of this invention, many variations of which are possible without departing from the spirit or scope thereof.

EXAMPLE I

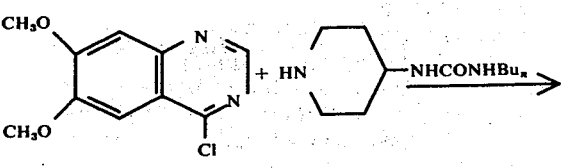

-continued

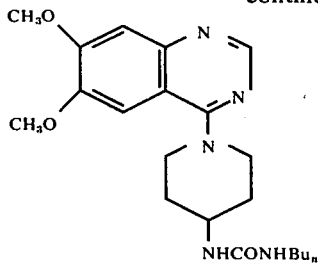

NHCONHBu<sub>n</sub>

The mono maleate salt was prepared by treating an alcoholic solution of the free base with an alcoholic solution of maleic acid. The precipitated salt was recrystallized (from EtOH) m.p. 195°–197° C.

The following compounds were prepared, using the method of Example 1, from the appropriate 4-chloroquinazoline derivative and amine, and were isolated in the form indicated. Both the theoretical and found analyses of the compounds are given, the found analyses being in parenthesis.

TABLE I

| Ex. | $R_1$ | R | Y | Position of Y and R in piperidine nucleus | Salt/Free Base/Hydrate m.p.° C | Analysis % (Found in brackets) C H N |
|---|---|---|---|---|---|---|
| 2 | H | H | —NHCOCH$_3$ | 4- | monohydrochloride monohydrate, 236 – 238° C | 53.05 6.55 14.56 (53.43 6.19 14.92) |
| 3 | CH$_3$ | H | —NHCONH(CH$_2$)$_3$CH$_3$ | 4- | monomaleate, 210 – 212° C | 58.01 6.82 13.53 (57.77 6.72 13.26) |
| 4 | H | H | —NHCOCH$_3$ | 3- | free base, 172 – 173° C | 61.80 6.71 16.96 (62.10 6.78 16.86) |
| 5 | H | H | —CH$_2$COOC$_2$H$_5$ | 4- | monohydrochloride, 192 – 194° C | 57.64 6.62 10.61 (57.13 6.52 10.73) |
| 6 | H | H | —NHCONH(CH$_2$)$_3$CH$_3$ | 3- | free base, 124 – 126° C | 61.99 7.54 18.08 (62.02 7.68 18.02) |
| 7 | CH$_3$CH$_2$ | H | —NHCONH(CH$_2$)$_3$CH$_3$ | 4- | ½hydrate, 154 – 156° C | 62.24 8.07 16.49 (62.14 7.92 16.34) |
| 8 | (CH$_3$)$_2$CH | H | —NHCONH(CH$_2$)$_3$CH$_3$ | 4- | monohydrochloride monohydrate, 205 – 209° C | 57.07 7.91 14.47 (56.78 7.45 14.38) |
| 9 | H | H | (benzimidazolinone group) | 4- | free base, 242 – 245° C | 65.17 5.72 17.27 (64.96 5.89 16.92) |

4-Chloro-6,7-dimethoxyquinazoline (45 g), 4-(3-n-butylureido)piperidine monhydrochloride (80 g) and triethylamine (140 ml) were refluxed in ethanol (450 ml) for 1¼ hours. The mixture was then concentrated in vacuo and the resultant solid was stirred in water which was then basified to pH 11 with 5N NaOH solution. The suspension was shaken with chloroform and the organic layer was separated, dried (Na$_2$CO$_3$) and evaporated to dryness in vacuo to give a yellow oily solid. Trituration with ether followed by recrystallization from ethanol gave 4-(4-[3-n-butylureido]-piperidino)-6,7-dimethoxyquinazoline (37 g). Small traces of impurities were removed by running a chloroform solution of the product down a glass column packed with "Florisil" and eluting with 10% isopropanol in chloroform. After evaporation, appropriate fractions were bulked and recrystallized from ethanol to give a pure product (21 g), m.p. 204°–5° C.

Anal. Calcd. for: C$_{20}$H$_{29}$N$_5$O$_3$: C, 62.0; H, 7.5; N, 18.1; Found: C, 62.1; H, 7.6; N, 18.3

EXAMPLE 10

Part A

Preparation of 4-[4-(2-pyridylmethyl amino)piperidino]-6,7dimethoxyquinazoline.

1-(6,7-Dimethoxyquinazolin-4-yl)piperid-4-one (2.9g) (which may be prepared as in part A of Example 91, hereinafter), and 2-aminomethylpyridine (1.19g) were refluxed together for two hours in benzene (50 ml.) in a flask fitted with a Dean and Stark trap. Ethanol (50 ml.) was added to the cooled solution followed by the slow addition of sodium borohydride (0.76g) with stirring. On completion of the addition stirring was continued for two hours followed by the addition of excess acetic acid. The mixture was poured into water, basified with 5N sodium hydroxide and was extracted with chloroform. Evaporation of the chloroform layer gave a yellow oil which solidified on trituration with ether. Recrystallization from ethyl acetate gave 4-[4-(2-pyridylmethyl-amino)piperidino]-6,7-dimethoxyquinazoline (2 g) m.p. 151°–155° C.

PART B

Preparation of 4-[4- 3-n-butyl-1-(2-pyridylmethyl-)ureido piperidino]-6,7-dimethoxyquinazoline.

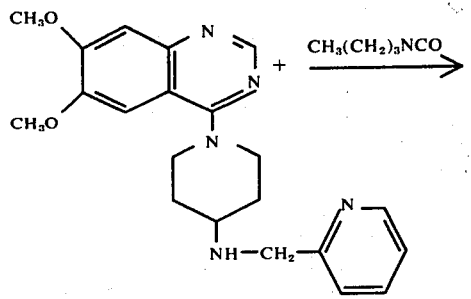

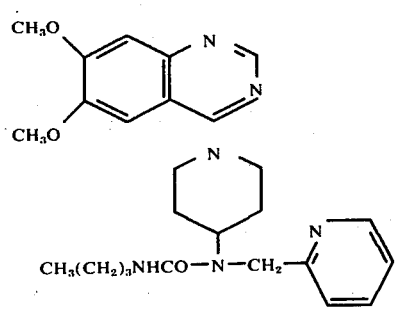

n-Butyl isocyanate (1 g) was added slowly to a stirred solution of 4-[4-(2-pyridylmethylamino)piperidino]-6,7-dimethoxyquinazoline, (1.4 g) prepared as in part A above, in dry chloroform, followed by standing at room temperature for 30 minutes. The solution was evaporated to dryness in vacuo to give a yellow oil which crystallized on trituration with ether. Recrystallization from ethyl acetate gave 4-[4-{3-n-butyl-1-(2-pyridylmethyl)ureido}piperidino]6,7-dimethoxyquinazoline (1.2 g) as pale yellow crystals, m.p. 162°–4° C.

Anal. Calcd. for $C_{26}H_{34}N_6O_3$: C, 65.25; H, 7.2; N, 17.6; Found: C, 65.2; H, 7.2; N, 17.4%

EXAMPLE 11

A. Preparation of 4-[4-(methylamino)piperidino]-6,7-dimethoxyquinazoline acetate.

1-(6,7-Dimethoxyquinazolin-4-yl)piperid-4-one (14.35 g — prepared as described in Exaple 91 Part A hereinafter) and ethanolic methylamine (33% w/w; 23.5 g) were stirred together in dry ethanol (150 ml) overnight. Sodium borohydride (2.0 g) was then added slowly under a nitrogen atmosphere with cooling. The mixture was then refluxed for 1 hour, cooled to room temperature and treated carefully with excess acetic acid. The mixture, after dilution with water and basification with 5N NaOH, was extracted with chloroform. After separation, the chloroform phase was dried ($MgSO_4$) and evaporated to give a crude oily product (10 g) which crystallized on trituration with a mixture of ethyl acetate and ether.

Recrystallization from acetonitrile and then ethyl acetate gave pure 4-[4-(Methylamino)piperidino]-6,7-dimethoxyquinazoline acetate, m.p. 169°–172°.

Anal. Calcd.: $C_{16}H_{22}N_4O_2.C_2H_4O_2$: C, 59.7; H, 7.2; N, 15.5% Found: C, 59.2; H, 7.5; N, 15.7%

B. Preparation of 4-[4-(1-methyl-3-n-propyl-ureido)-piperidino]-6,7-dimethoxyquinazoline.

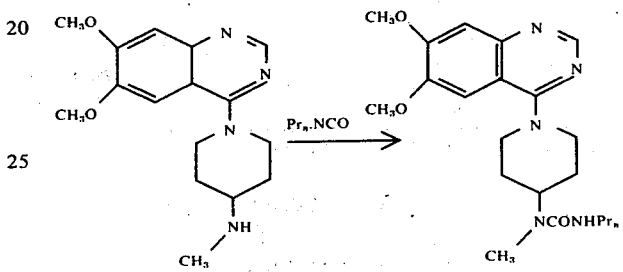

4-[4-(Methylamino)piperidino]-6,7-dimethoxyquinazoline (1.7 g) was dissolved in chloroform (10 mls.) and treated with n-propyl isocyanate (0.5 g). After standing overnight at room temperature the mixture was evaporated to dryness. The residue solidified on trituration with ethyl acetate. Recrystallisation from ethanol gave pure 4-[4-{1-methyl-3-n-propyl-ureido}piperidino]-6,7dimethoxyquinazoline (0.4 g) m.p. 209°–11°.

Anal. Calcd for: $C_{20}H_{29}N_5O_3.1/4H_2O$: C, 61.3; H, 7.6; N, 17.9%; Found: C, 61.3; H, 7.6; N, 17.4%

The following compounds were prepared, using the method of Examples 10 and 11, from the appropriate 4- piperidino -quinazoline and isocyanate or isothiocyanate, and isolated in the form indicated. In Example 18, sodium cyanate was used. Both the theoretical and found analyses of the products are given, the found analyses being in parentheses.

TABLE II

| Example | $R_1$ | R | Y | Position of Y and R in piperidine nucleus | Salt/Free Base/Hydrate m.p.° C | Analysis (Found in brackets) C H N |
|---|---|---|---|---|---|---|
| 12 | H | H | —NHCONHCH₃ | 4- | monomaleate; 205–207° C | 54.66 5.90 15.18 (54.95 5.76 14.78) |
| 13 | H | H | —NHCSNH(CH₂)₃CH₃ | 4- | monomaleate; 195–198° C | 55.47 6.40 13.48 (55.35 6.36 13.10) |
| 14 | H | H | —NHCONH(CH₂)₂CH₃ | 4- | Free base; 212–214° C | 61.10 7.29 18.75 (61.25 7.33 19.22) |
| 15 | H | H | —NHCONHCH₂CH₃ | 4- | Free base; 214–216° C | 60.15 7.01 19.49 (59.88 7.07 19.45) |

TABLE II-continued

[Structure: 6,7-dimethoxyquinazoline with 2-R₁ substituent and 4-piperidinyl group bearing Y and R substituents]

| Example | R₁ | R | Y | Position of Y and R in piperidine nucleus | Salt/Free Base/Hydrate m.p.° C | Analysis (Found in brackets) C  H  N |
|---|---|---|---|---|---|---|
| 16 | H | H | —NHCONH-Phenyl | 4- | Free base; 225–227° C | 64.85 6.18 17.19 (64.61 6.32 16.86) |
| 17 | H | H | —N—CH₂(4-Pyridyl) \| CONH(CH₂)₃CH₃ | 4- | Free base; 202–204° C | 65.25 7.16 17.56 (65.06 7.20 17.33) |
| 18 | H | H | —NHCONH₂ | 4- | Free base; 237.5–240° C | 57.99 6.39 21.13 (57.57 6.43 20.62) |
| 19 | H | H | —NHCONH(3-pyridyl) | 4- | dimaleate ½ hydrate; 132–144° C | 53.61 5.12 12.94 (53.31 5.14 12.98) |
| 20 | H | H | —N—CH₂(3-pyridyl) \| CONH(CH₂)₃CH₃ | 4- | Free base; 167–169° C | 65.25 7.16 17.56 (64.04 7.17 17.69) |
| 21 | H | H | —N—CH₂·Phenyl \| CONH(CH₂)₃CH₃ | 4- | Free base; 196–198° C | 67.90 7.39 14.66 (67.55 7.47 14.72) |
| 22 | H | H | —N—(3-pyridyl) \| CONH(CH₂)₃CH₃ | 4- | Free base; 175–177° C | 64.63 6.94 18.09 (64.57 7.22 18.09) |
| 23 | H | H | —N—(CH₂)₂N(CH₃)₂ \| CONH(CH₂)₃CH₃ | 4- | Free base; 140–142° C | 62.85 8.35 18.33 (62.95 8.40 18.31) |
| 24 | H | H | —NHCONHCH₂COOC₂H₅ | 4- | Free base; 209–211° C | 57.54 6.52 16.78 (57.70 6.56 16.50) |
| 25 | H | H | —N—CH₃ \| CONH(CH₂)₃CH₃ | 4- | Free base; 178–181° C | 62.82 7.78 17.44 (62.65 7.79 17.39) |
| 26 | H | H | —N—(CH₂)₂N—CH₂Ph \| \| CONH(CH₂)₃CH₃ (CH₂)₃CH₃ | 4- | Free base; 121–124° C | 68.72 8.39 14.57 (68.63 8.07 14.27) |
| 27 | H | H | —NCONHCH₃ \| (CH₂)₃CH₃ | 4- | Free base; 196–198° C | 62.82 7.78 17.44 (62.51 7.91 17.03) |
| 28 | H | H | —NCONH(CH₂)₃CH₃ \| (CH₂)₃CH₃ | 4- | Free base; 151–153° C | 64.98 8.41 15.79 (64.58 8.51 15.58) |
| 29 | H | H | —NCONHCH₂CH₃ \| CH₂·(4-pyridyl) | 4- | Free base; 232–235° C | 63.98 6.71 18.65 (63.87 6.85 18.46) |
| 30 | H | H | —NCONHCH₃ \| CH(CH₃)₂ | 4- | Free base; 186–188° C | 61.99 7.54 18.08 (61.25 7.59 18.19) |
| 31 | H | H | —NCONHCH₃ \| (CH₂)₂CH₃ | 4- | Free base; 204–207° C | 61.99 7.54 18.08 (61.23 7.63 17.83) |
| 32 | H | H | —NCONHCH₂CH₃ \| (CH₂)₂CH₃ | 4- | Free base; 174–176° C | 62.82 7.78 17.44 (63.01 7.28 17.49) |
| 33 | H | H | —NCONH(CH₂)₃CH₃ \| CH₂CH₂·(4-pyridyl) | 4- | Free base; 169–172° | 65.83 7.37 17.06 (65.80 7.38 17.23) |
| 34 | H | H | —NCONHCH₂CH₃ \| CH(CH₃)₂ | 4- | Free base; 174–175° | 62.82 7.78 17.44 (63.13 7.75 17.08) |
| 35 | H | H | —NCONH(CH₂)₂CH₃ \| CH(CH₃)₂ | 4- | Free base; 161–162° | 63.59 8.00 16.86 63.37 8.13 16.60) |
| 36 | H | H | —NCONH(CH₂)₃CH₃ \| CH₂CH₂·(2-pyridyl) | 4- | Free base ½ hydrate, 130–133° | 64.64 7.44 16.76 (64.48 7.44 16.80) |
| 37 | H | H | —NCONH(CH₂)₃CH₃ \| CH₂CH₃ | 4- | Free base; 155–159° | 63.59 8.00 16.85 (63.03 7.89 16.56) |
| 38 | H | H | —NCONHCH₂CH₃ \| CH₃ | 4- | Free base; 192–194° | 61.11 7.29 18.75 (61.46 7.29 18.62) |
| 39 | H | H | —NCONH(CH₂)₂CH₃ \| CH₂CH₃ | 4- | Free base; 173–175° | 62.82 7.78 17.44 (63.04 7.95 17.38 |

TABLE II-continued

| Example | $R_1$ | R | Y | Position of Y and R in piperidine nucleus | Salt/Free Base/Hydrate m.p.°C | Analysis (Found in brackets) C H N |
|---|---|---|---|---|---|---|
| 40 | H | H | —N.CONHCH$_2$CH$_3$ <br> \| <br> CH$_2$CH$_3$ | 4- | Free base; 182–184° | 61.99 7.54 18.07 <br> (63.08 7.59 17.99) |
| 41 | H | H | —NCSNHCH$_3$ <br> \| <br> CH$_3$ | 4- | Free base; 212–220° | 57.58 6.71 18.65 <br> (57.18 6.79 18.70) |
| 42 | H | H | —NCONH(CH$_2$)$_2$CH$_3$ <br> \| <br> CH$_2$CH$_2$OH | 4- | Free base; 161–165° | 60.41 7.48 16.77 <br> (60.10 7.63 16.81) |
| 43 | H | H | —NCSNH(CH$_2$)$_2$CH$_3$ <br> \| <br> CH$_3$ | 4- | Free base; 229–231° | 59.53 7.25 17.36 <br> (59.28 7.20 17.58) |

EXAMPLE 44

Preparation of 4-[4-(ethoxycarbonylamino)-piperidino]-6,7-dimethoxyquinazoline.

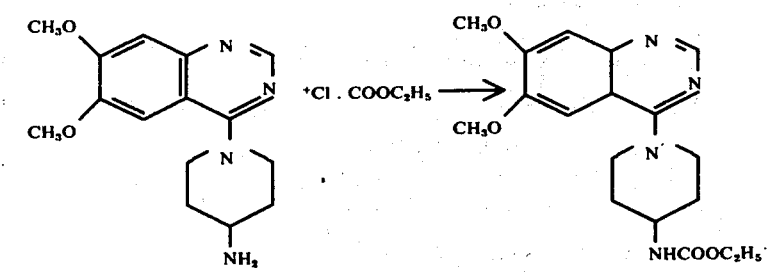

Part A

Preparation of 4-[4-amino piperidino]-6,7-dimethoxyquinazoline.

4-Chloro-6,7-dimethoxyquinazoline (0.9 g), 4-(trifluoroacetylamino)-piperidine hydrochloride (75% pure, 1.25 g) triethylamine (2.2 ml.) and ethanol (25 ml.) were refluxed together for aproximately 0.75 hr. The mixture was evaporated in vacuo to dryness followed by basification with aqueous 5N sodium hydroxide solution and extraction with chloroform. The chloroform extract was dried and evaporated in vacuo to give, after recrystallisation from ethanol 4-(4-trifluoroacetamido piperidino)-6,7-dimethoxyquinazoline (1.5 g) m.p. 217°–220° C.

Anal. Calcd for $C_{17}H_{19}F_3N_4O_3$: C, 50.7; H, 5.3; N, 13.9%; Found: C, 50.8; H, 4.75; N, 13.9

4-(4-Trifluoroacetamido piperidino)-6,7-dimethoxyquinazoline (59.5 g) 5N- sodium hydroxide solution (250 ml.) and tetrahydrofuran (500 ml.) were refluxed together with stirring for 2 1/2 hours. The T.H.F. layer was decanted off and concentrated to a small volume followed by treatment with water and extraction into CHCl$_3$.

Evaporation of the chloroform gave a yellow oil which on trituration with ether gave yellow crystals of 4-(4-aminopiperidino)-6,7-dimethoxyquinazoline (42 g) m.p. 133°–135° C.

Part B

4-[4-Aminopiperidino]-6,7-dimethoxyquinazoline prepared as in part A, (1.4 g), ethyl chloroformate (0.65 g) and triethylamine (1.1 ml.) were stirred together in dry chloroform (30 ml.) at room temperature for 1 hour. After concentration in vacuo the residue was suspended in water, basified with 5N sodium hydroxide solution and extracted with chloroform. The extract was dried (MgSO$_4$) and evaporated in vacuo to give the product as a pale yellow oily solid. The solid was re-dissolved in ethylacetate and converted to the tartrate salt by the addition of an ethanolic solution of tartaric acid. The tartrate was re-dissolved in hot ethanol and a small amount of impure material was allowed to crystallize out. The filtrate was taken, evaporated to dryness, rebasified in dilute aqueous sodium hydroxide solution and extracted with chloroform. Evaporation of the dried chloroform extract and recrystallization of the residue from ethylacetate gave 4-[4-(ethoxycarbonylamino)piperidino]-6,7-dimethoxyquinazoline (300 mg) m.p. 179°–181° C.

Anal. Calcd. for $C_{18}H_{24}N_4O_4$: C, 60.0; H, 6.7; N, 15.6; Found: C, 60.1; H, 6.8; N, 15.1%

The following compounds were prepared, using the method of Example 44, from the appropriate 4-(4-aminopiperidino)- or 4-(4-loweralkylaminopiperidino)-6,7-dimethoxyquinazoline, and the appropriate chloroformate (Examples 55 to 59 and 63), acyl chloride (Examples 46, 50 and 52), sulfonyl chloride (Examples 48, 49, 54 and 68), sulfamyl chloride Examples 47, 53, 62 and 64), carbamyl chloride (Examples 45 and 51), anhydride (Examples 65 and 67) and pyrocarbonate (Examples 60, 61 and 66 used (EtO.CO)$_2$O). The products were isolated in the form indicated. The theoretical and found analyses of the products are given, the found analyses being in parentheses.

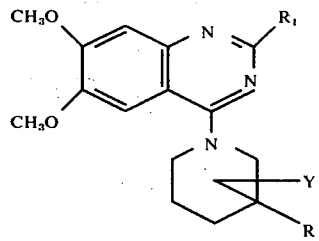

| Example | R$_1$ | R | Y | Position of Y in piperidine nucleus | Salt/Free Base/Hydrate m.p.° C | Analysis % (Found in brackets) C  H  N |
|---|---|---|---|---|---|---|
| 45 | H | H | —NHCON(CH$_3$)$_2$ | 4- | Free base; 178–183° C | 60.15 7.01 19.48 (59.63 7.13 18.95) |
| 46 | H | H | —NHCO(3-pyridyl) | 4- | Free base; 225–227° C | 64.11 5.89 17.80 (63.79 6.07 17.45) |
| 47 | H | H | —NHSO$_2$N(CH$_3$)$_2$ | 4- | Free base; 182–184° C | 51.64 6.37 17.71 (51.97 6.43 17.61) |
| 48 | H | H | —NHSO$_2$CH$_3$ | 4- | monohydrochloride monohydrate; 215–220° C | 45.66 5.98 13.31 (45.30 5.78 13.38) |
| 49 | H | H | —NHSO$_2$(3-pyridyl) | 4- | Free base; 222–225° C | 55.93 5.40 16.31 (56.19 5.23 16.61) |
| 50 | H | H | —NHCO(CH$_2$)$_3$CH$_3$ | 4- | monohydrochloride; 212–215° C | 58.74 7.15 13.70 (58.51 7.17 13.09) |
| 51 | H | H | —NHCON(C$_2$H$_5$)$_2$ | 4- | monohydrochloride ½-hydrate; 215–218° C | 55.48 7.22 16.18 (55.78 7.03 15.88) |
| 52 | H | H | —NHCOCH$_2$CH$_2$CH$_3$ | 4- | Free base; 157–159° C | 63.67 7.31 15.63 (63.99 7.55 15.24) |
| 53 | H | H | —NHSO$_2$NH(CH$_2$)$_2$CH$_3$ | 4- | Monohydrochloride ½-hydrate; 222–224° C | 47.51 6.42 15.39 (47.47 6.55 15.49) |
| 54 | H | H | —NHSO$_2$—⟨C$_6$H$_4$⟩—NHCOCH$_3$ | 4- | Mono p-toluene sulphonate; 241–244° C | 54.78 5.36 10.65 (54.55 5.46 10.57) |
| 55 | H | H | —NHCOO—⟨C$_6$H$_5$⟩ | 4- | Mono-maleate; 169–173° C | 59.54 5.38 10.68 (59.64 5.47 10.31) |
| 56 | H | H | —NHCOOCH$_3$ | 4- | Free base; 162–166° C | 58.95 6.40 16.17 (58.67 6.35 15.87) |
| 57 | H | H | —NHCOOCH$_2$CH(CH$_3$)$_2$ | 4- | Mono-maleate; 173–175° C | 57.13 6.39 11.10 (56.88 6.18 10.71) |
| 58 | H | H | —NHCOOCH$_2$—⟨C$_6$H$_5$⟩ | 4- | Oxalate; 198–203° C | 58.59 5.51 10.93 (58.19 5.57 11.32) |
| 59 | H | H | —NHCOO(CH$_2$)$_2$CH$_3$ | 4- | Oxalate ½-hydrate, 190–196° C | 53.27 6.17 11.83 (53.06 5.92 11.96) |
| 60 | H | H | —N(CH$_3$)COOCH$_2$CH$_3$ | 4- | Free base; 145–147° C | 60.95 7.00 14.96 (60.56 7.00 14.58) |
| 61 | H | H | —N(CH$_2$CH$_3$)COOCH$_2$CH$_3$ | 4- | Free base; 149–152° C | 61.84 7.27 14.42 (61.66 7.36 13.88) |
| 62 | H | H | —N(CH$_3$)SO$_2$NH(CH$_2$)$_2$CH$_3$ | 4- | Free base; 174–179° C | 53.88 6.90 16.54 (54.27 6.99 16.54) |
| 63 | H | H | —N(CH$_3$)COOCH$_2$CH(CH$_3$)$_2$ | 4- | Free base; 159–162° C | 62.67 7.51 13.92 (62.47 7.54 13.61) |
| 64 | H | H | —N(CH$_2$CH$_3$)SO$_2$NH(CH$_2$)$_2$CH$_3$ | 4- | monohydrochloride monohydrate, 174–189° C | 48.81 6.98 14.23 (48.90 6.72 14.02) |

-continued

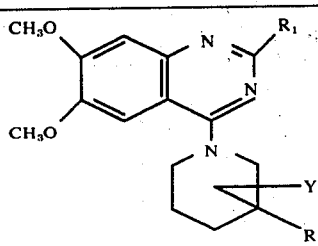

| Example | R₁ | R | Y | Position of Y in piperidine nucleus | Salt/Free Base/Hydrate m.p.° C | Analysis % (Found in brackets) C H N |
|---|---|---|---|---|---|---|
| 65 | H | H | —N(COCH₃)CH₃ | 4- | Free base; 177–180° C | 62.77 7.02 16.27 (62.36 7.09 16.03) |
| 66 | H | H | —N(COOCH₂CH₃)CH₂CH₂OH | 4- | Free base; 185–187° C | 59.39 6.98 13.85 (58.91 6.99 13.94) |
| 67 | H | H | —N(CO(CH₂)₂CH₃)CH₃ | 4- | Free base; 155–158° C | 64.49 7.58 15.04 (64.44 7.65 14.73) |
| 68 | H | H | —N(SO₂.(3-pyridyl))CH₃ | 4- | Free base; 183–187° C | 56.87 5.68 15.79 (57.27 5.61 15.90) |

EXAMPLE 69

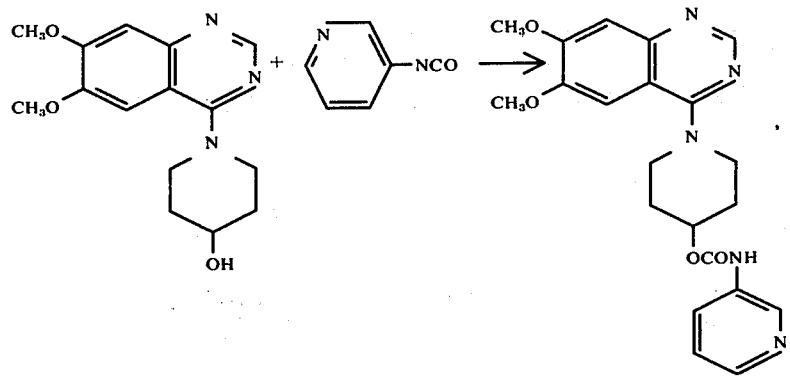

4-[4-Hydroxy piperidino]-6,7-dimethoxyquinazoline (2.9 g) and 3-pyridyl isocyanate (1.3 g) in 40 ml. of dry dioxane were heated together at 150° C in a stainless steel bomb for 24 hours. The cooled mixture was concentrated in vacuo to give a brown sticky solid which was triturated with ether and filtered. The insoluble residue was crystallized from acetonitrile to give 4-[4-(3-pyridylcarbamoyloxy)piperidino]-6,7-dimethoxyquinazoline (1.4 g) m.p. 180°–183° C.

Anal. Calcd. for $C_{21}H_{23}N_5O_4$: C, 61.3; H, 5.7; N, 17.1; Found: C, 61.3; H, 5.5; N, 17.5&

The following compounds were prepared, using the method of Example 69, from the appropriate 4-(4-hydroxypiperidino)quinazoline [or 4-(3-hydroxypyrrolidin-1-yl)-6,7-dimethoxyquinazoline in the case of Example 78] and the appropriate isocyanate (or sodium cyanate in the cae of Example 76), and the products were isolated in the form indicated. The theoretical and found analyses of the products are given, the found analyses being in parentheses.

TABLE IV

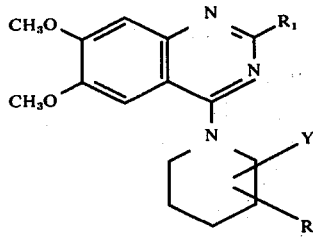

| | Position of Y in | Salt/Free Base/Hydrate | Analysis (Found in brackets) |

TABLE IV-continued

| Example | R₁ | R | Y | piperidine nucleus | m.p. ° C | C | H | N |
|---|---|---|---|---|---|---|---|---|
| 70 | H | H | —OCONHCH₃ | 4- | Free base; 195–198° C | 58.95 (59.05 | 6.40 6.47 | 16.17 16.19) |
| 71 | H | H | —OCONH(CH₂)₃CH₃ | 4- | Free base; 127–129° C | 61.84 (62.09 | 7.27 7.30 | 14.42 14.08) |
| 72 | H | H | —OCONH(CH₂)₂CH₃ | 4- | Free base; 164–167° C | 60.95 (61.00 | 7.00 6.98 | 14.96 15.29) |
| 73 | H | CH₃ | —OCONH(CH₂)₂CH₃ | 4- | Free base; 161–165° C | 61.84 (61.46 | 7.27 7.19 | 14.42 14.07) |
| 74 | H | H | —OCONHCH₂CH₃ | 4- | Free base; 168–170° C | 59.98 (59.98 | 6.71 6.76 | 15.55 15.45) |
| 75 | H | CH₃ | —OCONHCH₃ | 4- | Free base; 199–207° C | 59.98 (59.56 | 6.71 6.76 | 15.55 15.20) |
| 76 | H | H | —OCONH₂ | 4- | monohydrochloride, 232–235° C | 52.11 (51.90 | 5.74 5.78 | 15.19 15.00) |

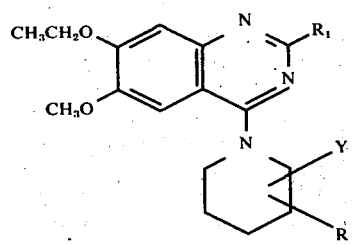

| Example | R₁ | R | Y | | | | | |
|---|---|---|---|---|---|---|---|---|
| 77 | H | H | —OCONHCH₂CH₃ | 4- | Free base; 286–288° C | 60.95 (60.71 | 7.00 7.12 | 14.96 14.71) |

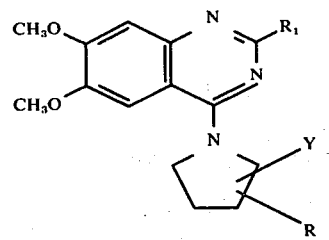

| | | | | | | Analysis % (Found in brackets) | | |
|---|---|---|---|---|---|---|---|---|
| Example | R₁ | R | Y | Position of Y in pyrrolidine nucleus | Salt/Free Base/Hydrate m.p.° C | C | H | N |
| 78 | H | H | —OCONH(CH₂)₂CH₃ | 3- | Free base; 186–189° C | 60.00 (59.97 | 6.71 6.94 | 15.55 15.66) |

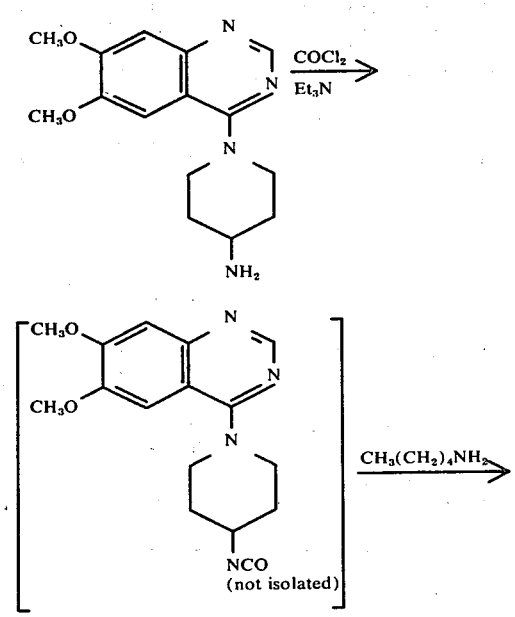

TABLE IV-continued

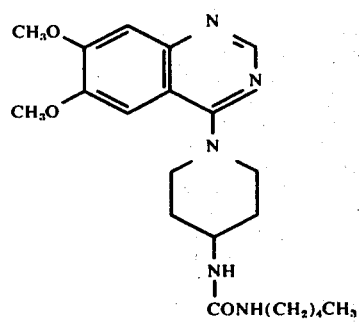

4-[4-Amino piperidino]-6,7-dimethoxyquinazoline (which may be prepared via the route of part A of Example 44) (5.8 g), triethyl amine (14 ml.) and chloroform (100 ml.) were added slowly to a solution of phosgene in toluene (48 ml. of 12 ½ w/v). The mixture was stirred at room temperature during the addition and then allowed to stand overnight. 1-Amino pentane (5.23 g) was then added slowly followed by standing for a further 24 hours. 2N hydrochloric acid (200 ml.) was added and the organic phase was collected and evaporated to dryness in vacuo to give an oil. The oil was dissolved in water, basified with 5N NaOH and extracted with chloroform. The extract was dried and evaporated in vacuo to give an oil which solidified on standing under petroleum ether. Recrystallization from acetonitrile gave 4-[4-(3-n-pentylureido)piperidino]-6,7-dimethoxyquinazoline (1.5 g) m.p. 192°–4° C.

Anal. Calcd. for $C_{21}H_{31}N_5O_3$: C, 62.8; H, 7.8; N, 17.4; Found: C, 62.4; H, 8.0; N, 17.8%

The following compounds were made, using the method of Example 79, from 4-(4-aminopiperidino)-6,7-dimethoxyquinazoline, phosgene, and the appropriate amine. The compounds were isolated in the form indicated, and the theoretical and found analyses are given, the found analyses being in brackets.

TABLE V

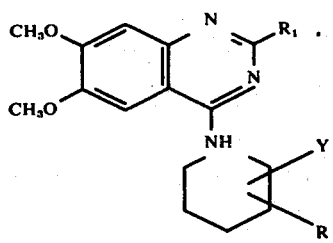

| Example | R₁ | R | Y | Position of Y in piperidine nucleus | Salt/Free Base/Hydrate m.p.°C | C | H | N |
|---|---|---|---|---|---|---|---|---|
| 80 | H | H | —NHCONH . CH₂CH(CH₃)₂ | 4- | monotartrate; 122–135° C | 53.62 (53.39 | 6.56 6.68 | 13.03 13.31) |
| 81 | H | H | —NHCO—N⟨piperidine⟩ | 4- | Dihydrochloride; 196–201° C | 53.39 (53.87 | 6.61 6.48 | 14.82 15.54) |
| 82 | H | H | —NHCONH(CH₂)₄OH | 4- | Free base; 131–145° C | 59.54 (58.96 | 7.24 7.04 | 17.36 16.97) |
| 83 | H | H | —NHCONH(CH₂)₂(2-pyridyl) | 4- | Free base; 199–201° C | 63.29 (63.26 | 6.47 6.37 | 19.25 18.96) |
| 84 | H | H | —NHCONHCH₂CH=CH₂ | 4- | Free base; 211–214° C | 61.44 (61.13 | 6.78 6.81 | 18.85 18.85) |
| 85 | H | H | —NHCONHCH₂C≡CH | 4- | monohydrate; 187–190° C | 58.90 (59.55 | 6.50 6.30 | 18.07 17.91) |

EXAMPLE 86

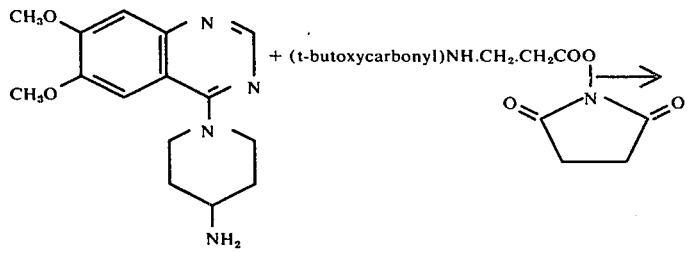

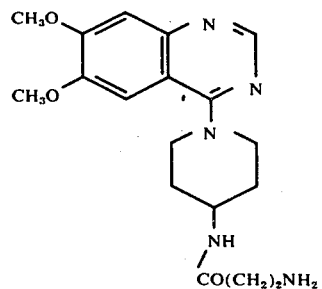

4-(4-Aminopiperidino)-6,7-dimethoxyquinazoline (which may be prepared via the route of part A of Example 44) (2.9 g) and N-[3-(-t-butoxycarbonylamino)propionyloxy]succinimide (2.9 g) were stirred for 2 hours at room temperature in dry chloroform (40 ml.). The mixture was filtered and the filtrate was treated with aqueous sodium carbonate solution (10% w/v) followed by separation of the organic phase which was dried ($Na_2CO_3$) and evaporated to dryness in vacuo. The t-butoxycarbonyl group was then removed by dissolving the residue in methanol (40 ml.) followed by refluxing for 4 hours with the addition of 2N aqueous HCl (12 ml.). The mixture was evaporated to dryness in vacuo and the residual hydrochloride was rebasified (5N NaOH) and extracted into chloroform. The concentrated chloroform solution was passed down a column packed with "Florisil"(in chloroform) followed by elution with chloroform-methanol. Appropriate fractions were bulked and evaporated in vacuo to give crude 4-(4-[β-aminopropionamido]-piperidino)6,7-dimethoxyquinazoline which was dissolved in ethanol an converted to the dimaleate salt by treatment with a solution of maleic acid in ispropanol. Recrystallization from acetonitrile gave the pure dimaleate (500 mg.) m.p. 166°–170° C.

Anal. Calcd. for $C_{18}H_{25}N_5O_3 \cdot 2C_4H_4O_4$: C, 52.8; H, 5.6; N, 11.8; Found: C, 51.9; H, 5.6; N, 11.7%

EXAMPLE 87

Using the method of Example 86, but starting from 4-[4-aminopiperidino]-6,7-dimethoxyquinazoline and N-[2-(t-butoxy carbonylamino)isovaleryloxy]succinimide, and using hydrochloric acid instead of maleic acid in the penultimate step, 4-(4-[α-amino-isovaleramido]piperidino-6,7-dimethoxyquinazoline dihydrochloride dihydrate was isolated, m.p. 218°–222° C.

Anal. Calcd. for $C_{20}H_{29}N_5O_3$: C, 48.38; H, 7.11; N, 14.11%; Found: C, 49.23; H, 6.86; N, 13.78%

EXAMPLE 88

Using the method of Example 86, starting from N-(α-methoxyacetyloxy)-succinimide and 4-(4-aminopiperidino)-6,7-dimethoxyquinazoline, 4-(4-(α-methoxyacetamido)piperidino]-6,7-dimethoxyquinazoline was prepared, m.p. 133°–135° C.

Anal. Calcd. for $C_{18}H_{24}N_4O_4$: C, 59.98; 6.71; N, 15.55%; Found: C, 59.77; H, 6.82; N, 15.15%

EXAMPLE 89

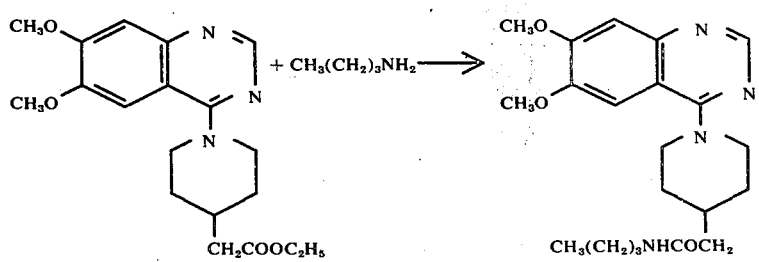

4-[4-Ethoxycarbonylmethyl)piperidino]-6,7-dimethoxyquinazoline (which may be prepared as in Example 5) (5 g) and n-butylamine (10 ml) were heated together at about 78° C for 22 hours. The mixture was cooled, basified and extracted with chloroform. The extract was dried and evaporated to dryness in vacuo to give an oil which on dissolution in ether crystallized as a white solid. Recrystallization from ethyl acetate gave 4-[4-(n-butylcarbamoylmethyl)piperidino]-6,7-dimethoxyquinazoline (710 mg) m.p. 142°–4° C.

Anal. Calcd. for $C_{21}H_{30}N_4O_3$: C, 65.3; H, 7.8; N, 14.5; Found: C, 64.9; H, 8.01; N, 14.25%

EXAMPLE 90

Part A

Preparation of 4-(4-[α-bromoacetamido]-piperidino)-6,7-dimethoxyquinazoline.

4-(4-Aminopiperidino)-6,7-dimethoxyquinazoline (2.9 g) (which may be prepared via the route of Example 44 part A), and triethylamine (1.5 g) in dry chloroform (20 ml.) were treated wih α-bromoacetyl bromide (2.3 gm) to obtain a mixture containing 4-(4-[α-bromoacetamido]piperidino)-6,7-dimethoxyquinazoline.

Part B

Preparation of 4-[4-(α-piperidinoacetamido)-piperidino]-6,7-dimethoxyquinazoline ditartrate.

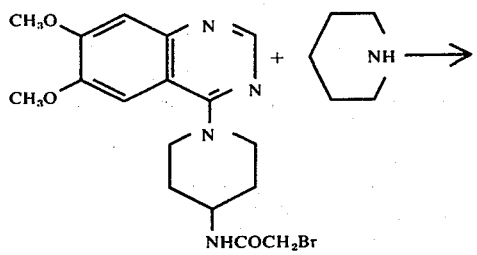

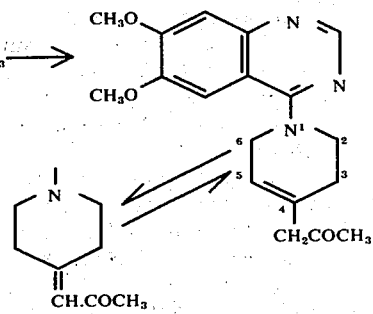

The mixture prepared in part A was stirred for 30 minutes at room temperature and then piperidine (1.0 gm) was added. After stirring for 3 hours at room temperature the mixture was treated with sodium carbonate solution and the chloroform layer was separated, washed, dried and evaporated to dryness in vacuo to give an oil. The oil was dissolved in isopropanol and converted to the ditartrate by reaction with tartaric acid. Recrystallization from ethanol gave 4-[4-(α-piperidino acetamido)piperidino]-6,7-dimethoxyquinazoline ditartrate (1.35 g) m.p. 138°–141° C.

Anal. Calcd. $C_{22}H_{31}N_5O_3.2C_4H_6O_6$: C, 50.5; H, 6.1; N, 9.8; Found: C, 50.9; H, 6.3; N, 9.9%

EXAMPLE 91

Part A

Preparation of 4-(4-oxopiperidino)-6,7-dimethoxyquinazoline.

4-Chloro-6,7-dimethoxyquinazoline (30 g), 4-piperidone ethylene ketal hydrochloride (25 g), triethylamine (35 g) and ethanol (250 ml.) were refluxed together for 3 hours. Aqueous sodium carbonate was added followed by extraction with chloroform after which the chloroform extract was dried and evaporated in vacuo to give an oil. The oil was redissolved in aqueous hydrochloric acid (1.5N, 200 ml.) and refluxed for 2 hours followed by cooling, basification ($Na_2CO_3$ 10% $sol_n$) and extraction into chlororform. Evaporation of the dried chloroform extract gave 4-(4-oxopiperidino)-6,7-dimethoxyquinazoline (37.6 g) m.p. 176°–8° C.

Part B

Preparation of 4-[4-acetonyl-1,2,3,6-tetrahydropyrid-1-yl]-6,7-dimethoxyquinazoline monomaleate.

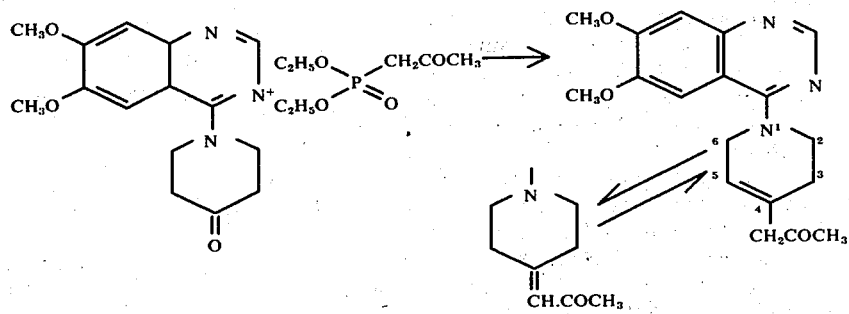

Diethyl acetonylphosphonate in dry dimethoxy ethane (D.M.E.) (50 ml.) was added slowly to a stirred suspension of sodium hydride (1 g, 80% oil dispersed) in D.M.E. (50 ml.) followed by stirring at room temperature for 30 minutes. 4-(4-oxopiperidino-6,7-dimethoxyquinazoline prepared in part A 8.8 g) in D.M. E. (100 ml.) was added rapidly followed by heating at 80° C for 1 hour. The solution was poured into ice-water and extracted with chloroform. The organic layer was separated, dried an concentrated in vacuo to give an oil which was dissolved in toluene and converted to the maleate by treatment with ethereal maleic acid. Recrystallization from ethanol gave 4-[4-acetonyl-1,2,3,6-tetrahydro-pyrid-1-yl]-6,7-dimethoxyquinazoline monomaleate, m.p. 179°–181° C.

Anal. Calcd. for $C_{17}H_{21}N_3O_3.C_4H_4O_4$: C, 59.6; H, 5.7; N, 9.5; Found: C, 58.7; H, 5.7; N, 9.3%

The following compound was prepared, using the method of Example 91, from 4-(4-oxo piperidino)-6,7-dimethoxyquinazoline and diethyl ethoxycarbonylmethylphosphonate, the product being isolated in the form indicated. The theoretical and found analysis of the compound are given, the found analysis being in parentheses.

TABLE VI

[Structure: 6,7-dimethoxyquinazoline with tetrahydropyridinyl group bearing Y substituent, and R₁ at the 2-position]

| Example | R₁ | Y | Salt/Free Base m.p.° C | Analysis (Found in brackets) C H N |
|---------|----|----|------------------------|-------------------------------------|
| 92 | H | —$CH_2COOC_2H_5$ | Free base; 133–135° C | 63.85 6.48 11.76 (63.50 6.65 11.47 |

EXAMPLE 93

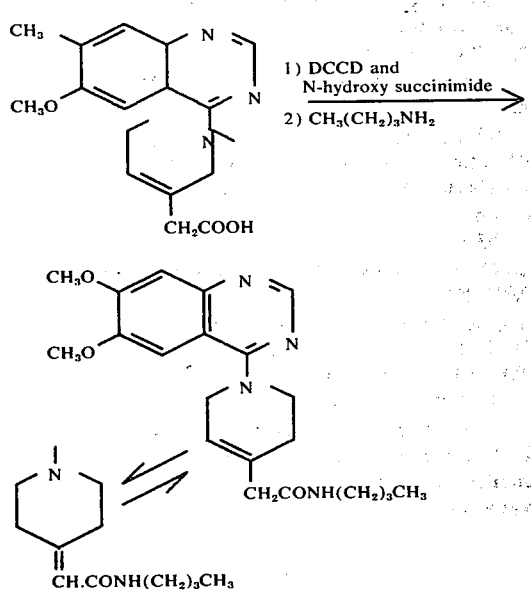

4-(4-[Carboxymethyl]-1,2,3,6-tetrahydropyrid-1-yl)-6,7-dimethoxyquinazoline hydrochloride (0.92 g) (prepared by hydrolysis of the ester of Example 92) in dry chloroform (20 ml.) containing triethylamine (0.3 g) was stirred until complete solution occurred. Dicyclohexylcarbodiimide (0.63 g) and N-hydroxy-succinimide (0.35 g) were added followed by standing overnight during which time a white solid precipitated. n-Butylamine (0.22 g) was added and the mixture again left to stand (5 hours) after which the solution was filtered, washed with water and the organic phase evaporated to dryness in vacuo. The residue was triturated with acetonitrile, filtered and the filtrate was treated with ethereal HCl until acid. The precipitated hydrochloride of 4-[4-(n-butylcarbamoylmethyl)-1,2,3,6-tetrahydropyrid-1-yl]-6,7-dimethoxyquinazoline was recrystallized from ethanol (yielded 340 mg) m.p. 196° (as a hemihydrate).

Anal. Calcd. for $C_{21}H_{28}N_4O_3 \cdot HCl \cdot 1/2H_2O$: C, 58.65; H, 7.0; N, 13.0; Found: C, 58.2; H, 6.6; N, 12.9%

EXAMPLE 94

The following is an Example of a typical parenteral formulation, intended for intravenous injection, in which the active ingredient is the compound of Example 1.

| | mg/ml |
|---|---|
| Active ingredient | 5.0 |
| Sodium chloride | 8.5 |
| Hydrochloric acid | Sufficient for pH adjustment |
| Water | Sufficient to bring correct volume |

The active ingredient and sodium chloride are dissolved in a little of the hydrochloric acid, and more of the latter is added until the pH of the solution is within the limits 3.75± 0.25, and the volume as nearly approaches the desired final volume as possible. Water is then added to bring the volume to the appropriate volume for the active ingredient and the salt to be present at the desired concentrations.

What is claimed is:

1. A compound selected from the group consisting of

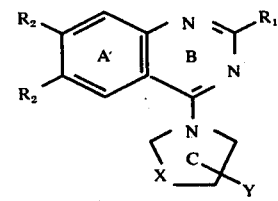

and the pharmaceutically acceptable acid addition salts thereof, wherein $R_1$ is selected from the group consisting of hydrogen and alkyl having from one to three carbon atoms;

$R_2$ is alkoxy having from one to two carbon atoms;

X is selected from the group consisting of —CH═CH—, and alkylene having from one to two carbon atoms; and Y is a substituent at the 3- or 4-position of ring C selected from the group consisting of —$Z_1COR_3$, —$N(R_4)SO_2R_5$, —$Z_2CONR_6R_7$ and $Z_2CSNR_6R_7$ wherein $Z_1$ is selected from the group consisting of $-CH_2-$ and $-N(R_4)-$; $R_3$ is selected from the group consisting of alkyl having from one to four carbon atoms, alkoxy having from one to four carbon atoms, benzyloxy, phenoxy, ethoxy-carbonylmethyl and pyridyl; $R_5$ is selected from the group consisting of alkyl having from one to four carbon, pyridyl and $-NR_6R_7$; $Z_2$ is selected from the group consisting of $-O-$, $-CH_2-$ and $-N(R_4)-$ wherein $R_4$ is selected from the group of hydrogen, pyridyl, phenyl, alkyl having from one to four carbon atoms and substituted said alkyl wherein said substituent is selected from the group consisting of amino, dimethylamino, hydroxy, pyridyl and phenyl; and $R_6$ and $R_7$ when considered separately are each selected from the group consisting of hydrogen, alkyl having one to four carbon atoms and $R_6$ and $R_7$ when considered together with the nitrogen to which they are attached form a piperidine ring, with the proviso that when X is $-CH=CH-$ or $-CH_2CH=CH-$ Y is selected from the group consisting of $-CH_2COR_3$, $-CH_2CONR_6R_7$ and $-CH_2CSNR_6R_7$.

2. A compound of claim 1 where $R_1$ is hydrogen, $R_2$ is methoxy, X is $-CH_2CH_2-$ and Y is a substituent at the 4-position.

3. A compound of claim 2 wherein Y is $Z_1COR_3$ wherein $Z_1$ is $-N(R_4)-$ wherein $R_4$ is selected from the group consisting of hydrogen and alkyl having from one to four carbon atoms, and $R_3$ is selected from the group consisting of alkyl having from one to four carbon atoms and alkoxy having from one to four carbon atoms.

4. The compound of claim 3 wherein Y is $-NHCO_2CH_2CH_3$.

5. The compound of claim 3 wherein Y is $-N(CH_3)CO_2CH_2CH_3$.

6. The compound of claim 3 wherein Y is $-NHCO_2CH_2CH(CH_3)_2$.

7. The compound of claim 3 wherein Y is $-NHCO_2(CH_2)_2CH_3$.

8. The compound of claim 3 wherein Y is $-N(CH_2CH_3)CO_2CH_2CH_3$.

9. The compound of claim 3 wherein Y is $-N(CH_3)CO(CH_2)_2CH_3$.

10. The compound of claim 3 wherein Y is $-NHCO(CH_2)_2CH_3$.

11. A compound of claim 2 wherein Y is $-N(R_4)SO_2R_5$ wherein $R_4$ is selected from the group consisting of hydrogen and alkyl having from one to four carbon atoms, and $R_5$ is selected from the group consisting of pyridyl and $-NR_6R_7$ wherein $R_6$ and $R_7$ when considered separately are each selected from the group consisting of hydrogen and alkyl having from one to four carbon atoms.

12. The compound of claim 11 wherein Y is $-N(CH_3)SO_2NH(CH_2)_2CH_3$.

13. The compound of claim 11 wherein Y is $-NHSO_2NH(CH_2)_2CH_3$.

14. The compound of claim 11 wherein Y is $-NHSO_2-(3-pyridyl)$.

15. The compound of claim 11 wherein Y is $-N(CH_3SO_2-(3-pyridyl)$.

16. A compound of claim 2 wherein Y is $Z_2CONR_6R_7$ wherein $Z_2$ is selected from the group consisting of $-O-$ and $-N(R_4)-$ and $R_6$ and $R_7$ when considered separately are each selected from the group consisting of hydrogen and alkyl having from one to four carbon atoms, and $R^4$ is selected from the group consisting of hydrogen, alkyl of one to four carbon atoms and pyridyl-substituted alkyl.

17. The compound of claim 16 wherein Y is $-N(CH_2CH_2-[4-pyridyl]) COHN-(CH_2)_3CH_3$.

18. The compound of claim 16 wherein Y is $-N([CH_2]_3CH_3)CONHCH_3$.

19. The compound of claim 16 wherein Y is $-N([CH_2]_3CH_3)CONH(CH_2)_3CH_3$.

20. The compound of claim 16 wherein Y is $-O-CONHCH_2CH_3$.

21. The compound of claim 16 wherein Y is $-O-CONH(CH_2)_2CH_3$.

22. The compound of claim 16 wherein Y is $-NHCONH(CH_2)_3CH_3$.

23. The compound of claim 16 wherein Y is $-N(CH_3)CONH(CH_2)_2CH_3$.

24. A method of stimulating the heart of an animal which comprises administering to said animal a cardiac stimulating amount of a compound selected from the group of claim 1.

* * * * *

UNITED STATES PATENT AND TRADEMARK OFFICE
CERTIFICATE OF CORRECTION

PATENT NO. : 4,001,422
DATED : JANUARY 4, 1977
INVENTOR(S) : JOHN C. DANILEWICZ ET AL

It is certified that error appears in the above-identified patent and that said Letters Patent are hereby corrected as shown below:

The formula at Col. 33, lines 25-33 should read:

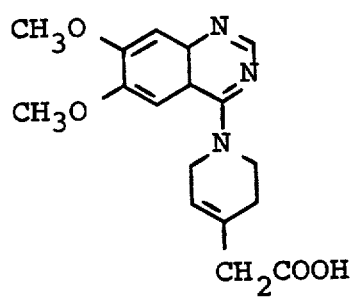

Col. 36, line 28, "COHN" should read -- CONH --.

Signed and Sealed this

Fourteenth Day of June 1977

[SEAL]

Attest:

RUTH C. MASON
Attesting Officer

C. MARSHALL DANN
Commissioner of Patents and Trademarks